US011703579B2

(12) United States Patent
Imai et al.

(10) Patent No.: US 11,703,579 B2
(45) Date of Patent: *Jul. 18, 2023

(54) METHOD AND APPARATUS FOR SELECTING POWER STATES IN AN ULTRASOUND IMAGING SYSTEM

(71) Applicant: FUJIFILM SONOSITE, INC., Bothell, WA (US)

(72) Inventors: Yoshiro Imai, Ashigarakami-gun (JP); Richard Hippe, Snohomish, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 49 days.

This patent is subject to a terminal disclaimer.

(21) Appl. No.: 17/220,762

(22) Filed: Apr. 1, 2021

(65) Prior Publication Data

US 2021/0223375 A1 Jul. 22, 2021

Related U.S. Application Data

(63) Continuation of application No. 16/046,853, filed on Jul. 26, 2018, now Pat. No. 10,989,798.

(51) Int. Cl.
*G01S 7/52* (2006.01)
*G01S 15/89* (2006.01)
(Continued)

(52) U.S. Cl.
CPC ....... *G01S 7/52096* (2013.01); *G01S 15/8911* (2013.01); *G06F 1/206* (2013.01); *G06F 1/3234* (2013.01)

(58) Field of Classification Search
CPC ............. G01S 7/52096; G01S 15/8911; G01S 7/5205; G01S 7/5208; G06F 1/206;
(Continued)

(56) References Cited

U.S. PATENT DOCUMENTS 10,989,798 B2* 4/2021 Imai ...................... A61B 8/429
2009/0043203 A1 2/2009 Pelissier et al.
(Continued)

FOREIGN PATENT DOCUMENTS

EP 3138499 A1 3/2017
EP 3826541 A1 * 6/2021 ............. A61B 8/469
(Continued)

OTHER PUBLICATIONS

Extended European Search Report on the Patentability of Application No. 18927674.4 dated Mar. 23, 2022, 8 pages.
(Continued)

*Primary Examiner* — Daniel Pihulic
(74) *Attorney, Agent, or Firm* — Womble Bond Dickinson (US) LLP

(57) ABSTRACT

An ultrasound imaging system includes a processor that is programmed to operate the system in a normal operating state and two or more lesser power states. The processor lowers the operating power state to a lesser power state upon detecting one or more operating conditions such as no tissue been imaged in a predetermined time limit or that the imaging system or transducer has not been moved in a time limit. Upon awakening from a power off state, the processor implements a lesser power state before operating at the normal operating state to avoid undue power use until the transducer is positioned to image tissue.

19 Claims, 4 Drawing Sheets

(51) Int. Cl.
*G06F 1/20* (2006.01)
*G06F 1/3234* (2019.01)

(58) Field of Classification Search
CPC .... G06F 1/3234; G06F 1/3206; G06F 1/3296; A61B 8/429; A61B 8/469; A61B 8/546; A61B 8/56; Y02D 10/00
See application file for complete search history.

(56) References Cited

U.S. PATENT DOCUMENTS

| | | | |
|---|---|---|---|
| 2017/0303899 A1 | 10/2017 | Willsie | |
| 2020/0033461 A1* | 1/2020 | Imai | G06F 1/3206 |
| 2021/0137492 A1* | 5/2021 | Imai | A61B 8/5207 |
| 2021/0223375 A1* | 7/2021 | Imai | A61B 8/546 |

FOREIGN PATENT DOCUMENTS

| | | | | |
|---|---|---|---|---|
| JP | 2003235845 A | 8/2003 | | |
| JP | 2010227357 A | 10/2010 | | |
| JP | 2017513650 A | 6/2017 | | |
| WO | 2008146208 A2 | 12/2008 | | |
| WO | WO-2020023075 A1 * | 1/2020 | ............. | A61B 8/469 |
| WO | WO-2021014767 A1 * | 1/2021 | ............... | A61B 8/06 |

OTHER PUBLICATIONS

Japanese Office Action and Search Report on the Patentability of Application No. 2020-571637 dated Jan. 4, 2022, 6 pages.
Japanese Office Action and Search Report on the Patentability of Application No. 2020-571637 dated Jul. 25, 2022, 6 pages.

* cited by examiner

METHOD AND APPARATUS FOR SELECTING POWER STATES IN AN ULTRASOUND IMAGING SYSTEM

The present application is a continuation of U.S. patent application Ser. No. 16/046,853, titled "METHOD AND APPARATUS FOR SELECTING POWER STATES IN AN ULTRASOUND IMAGING SYSTEM" filed on Jul. 26, 2018 and which is incorporated herein by reference in its entirety.

TECHNICAL FIELD

The present invention relates to ultrasound imaging systems and in particular to systems for conserving power in ultrasound imaging systems.

BACKGROUND

As the processing power of integrated circuits increases, medical devices in general and ultrasound imaging systems in particular have been become smaller and more portable. Ultrasound imaging systems are now small enough that they can be easily carried and powered by rechargeable batteries. Despite advances in battery technology, there is always a need to reduce the power consumption of such devices to increase the operating and standby time. While electronic systems are known that selectively power down when not being used, these systems can be accidentally awakened and can consume battery power when they are not actively being used.

SUMMARY

As will be explained below, the technology described herein relates to systems and methods for increasing the operating and/or standby time of an ultrasound imaging system by reducing the power drawn when the one or more operating conditions are detected such as the system not actively imaging tissue, the system being immobile for a period of time or a transducer probe being warmer than permitted. In some embodiments, an ultrasound imaging system operates in a number of different power states including a normal operating state and two or more lesser power states. Upon awakening, the system begins operating in a lesser power state before operating in the normal operating state. In some embodiments, the normal operating state is only entered if an ultrasound transducer is being used to actively capture images of tissue. In some embodiments, an initial "power on" of the imaging system first operates in a lesser power state until tissue is detected.

DETAILED DESCRIPTION

As will be explained in detail below, the technology described herein relates to medical devices and in particular to ultrasound imaging systems having a number of different operating power levels or operating states that reduce the power used by the system when it is not actively imaging tissue, is not being moved or has exceeded a thermal threshold. One or more processors in the system are configured to detect when an imaging transducer is not being used to actively image tissue or when the system has not been moved for more than a predetermined period of time. The one or more processors cause the ultrasound imaging system to enter a lesser power state that draws less power than used in a normal operating state, Upon waking up, the system begins operating the system in a lesser power state before proceeding to the normal operating state when tissue is being imaged.

Figure 1:
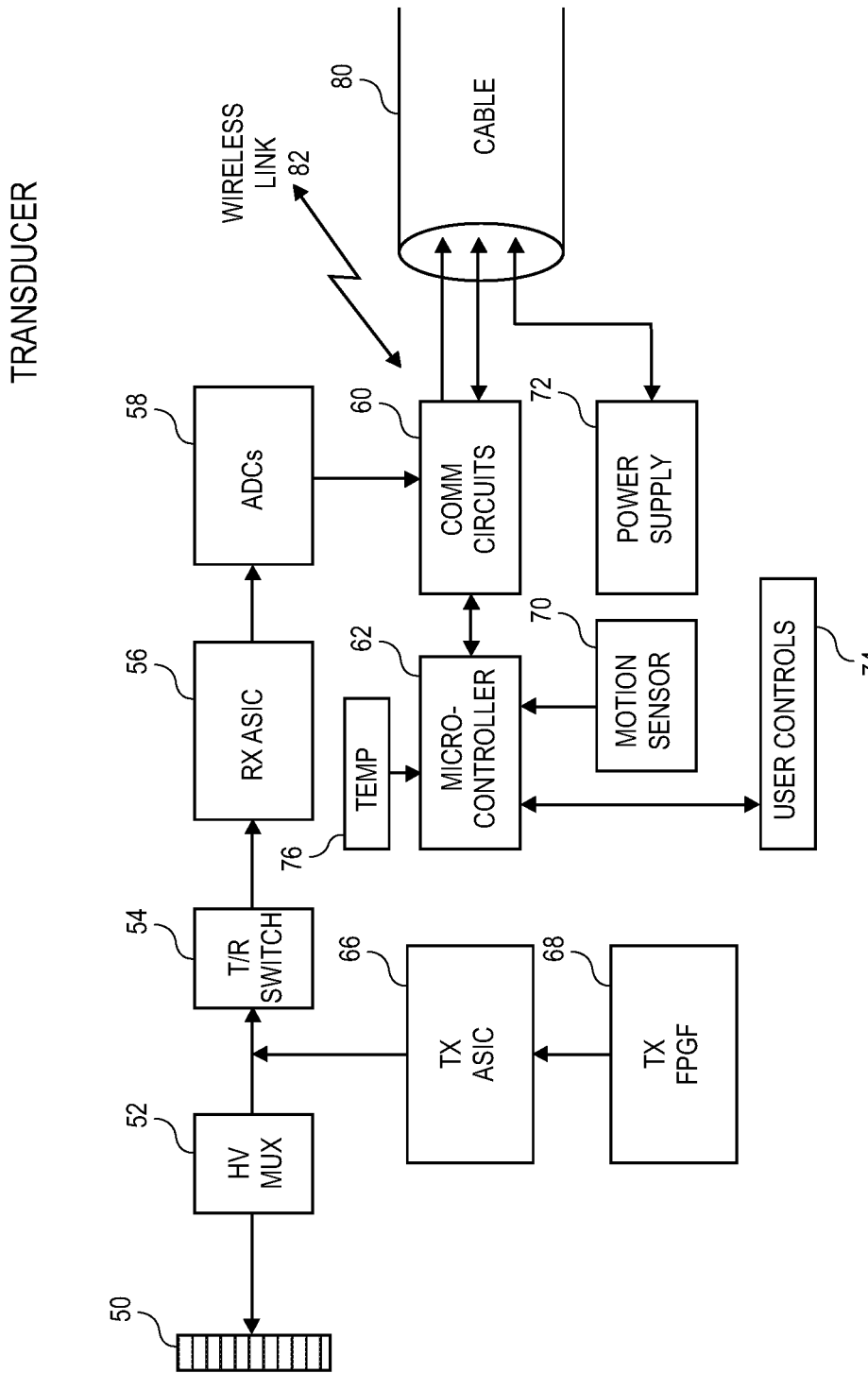
FIG. 1 is a block diagram of an ultrasound imaging transducer in accordance with one embodiment of the disclosed technology.

FIG. 1 shows a simplified block diagram of an ultrasound imaging transducer in accordance with some embodiments of the disclosed technology. The transducer preferably includes an arrangement of piezoelectric transducer elements 50, which can be a 1D, 1.50 or 2D linear, curved or a phased array of PZT or other piezoelectric elements that are constructed to produce ultrasound energy and direct the energy into a body and to receive corresponding acoustic echo signals. In some embodiments, the array is designed to produce ultrasound in a single bandwidth of frequencies around a center frequency but in other embodiments, the transducer can be configured to produce ultrasound around two or more center frequencies (e.g. dual mode imaging). Typically, there are more piezoelectric transducer elements than the number of transmit (TX) and receive (RX) channels in the ultrasound imaging system. Therefore, a high voltage multiplexer 52 is used to connect a number of transmit and receive channels to selected transducer array elements. A transmit/receive switch 54 serves to disconnect sensitive receive electronics during the time when high voltage transmit pulses are being applied to the transducer elements during pulse firing. A receive (RX) application specific integrated circuit (ASIC) 56 receives analog echo signals produced by the transducer elements and conditions them for further processing. Such processing can include such steps as filtering and amplification. The output of the receive ASIC 56 is provided to a bank of analog to digital converters 58 that convert the analog echo signals into corresponding digital signals.

Digitized echo signals are routed to a communication circuit 60 for transmission to a base unit of the imaging system (FIG. 2) via a wired communication link in a cable 80 or via a wireless communication link 82. A microcontroller 62 controls the operation of the transducer. The microcontroller 62 operates a transmit (TX) FPGA 68 that controls the manner and timing in which driving signals are applied to individual transducer elements. Driving signals from the TX FPGA 68 are supplied to a transmit (TX) ASIC 66 that conditions and boosts the voltage of the driving signals in order to cause the transducer elements to produce the acoustic ultrasound signals for delivery into a region of interest.

Also connected to the microcontroller 62 is a motion sensor 70 that detects if the transducer is being moved and the angle at which the transducer is being held. Such a motion sensor 70 can be an accelerometer, integrated circuit, or other device that detects movement and gravity. In some embodiments, the transducer includes one or more user controls 74 (buttons, knobs, touch sensitive pad etc.) that a user can interact with to operate the imaging system. Commands entered by interacting with the user controls 74 are transmitted to the base unit of the imaging system via the wired or wireless communication link.

A power supply 72 powers the electronics in the transducer. The power supply 72 can either receive power from the base unit through the cable 80 that connects the transducer to the base unit. Alternatively, the power supply 72 can include one or more rechargeable batteries (not shown). The amount of power supplied by or drawn from the power supply 72 is discussed in further detail below.

A temperature sensor 76 (e.g. thermistor) produces a signal to the microcontroller 62 that is indicative of the temperature of the transducer.

Figure 2:
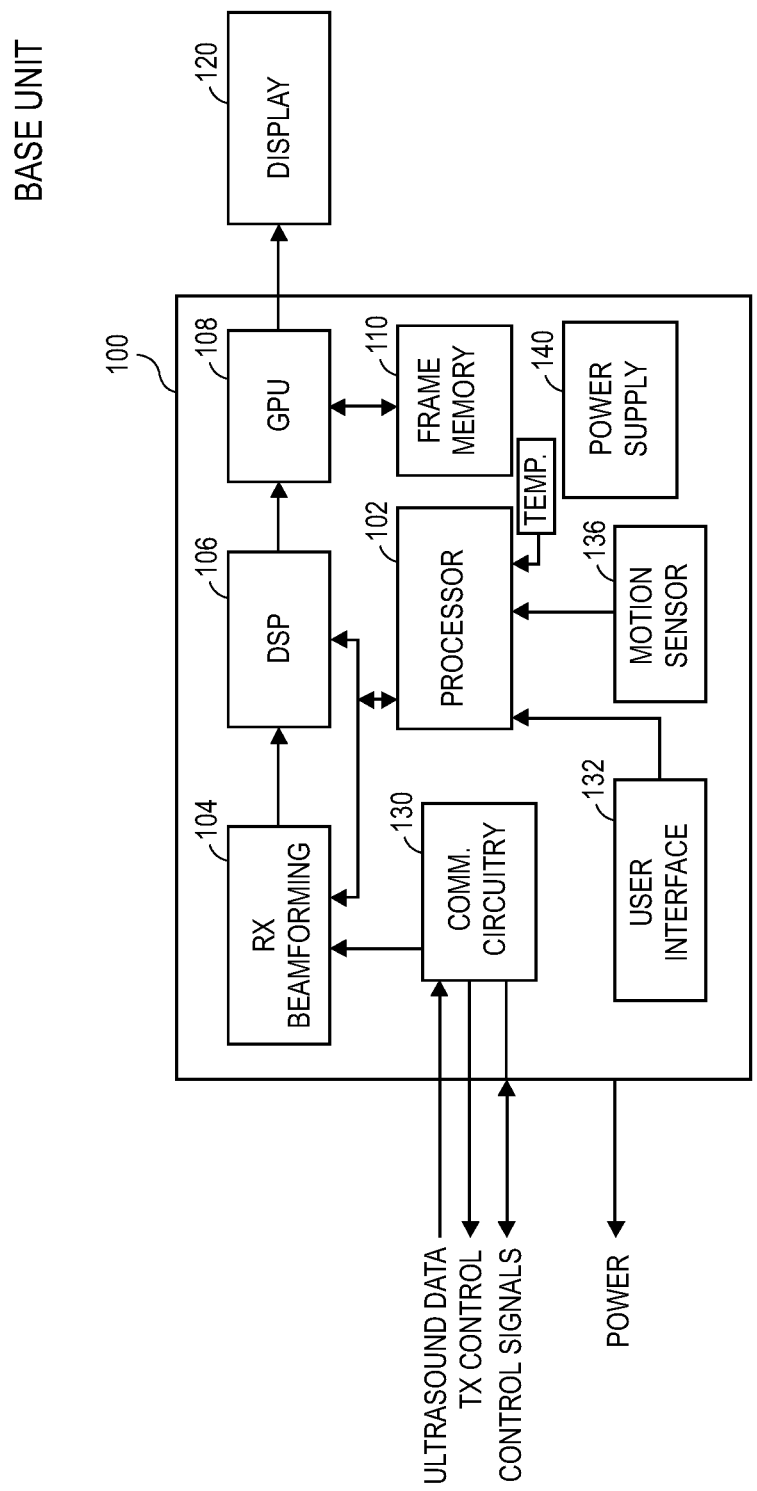
FIG. 2 is a block diagram of a base unit of an ultrasound imaging system in accordance with one embodiment of the disclosed technology.

FIG. 2 shows a simplified block diagram of a base unit for an ultrasound imaging system in accordance with an embodiment of the disclosed technology. The base unit includes one or more processors 102 (CPU, DSP, GPU or combination thereof) that are configured to execute program instructions stored in a non-volatile computer readable memory to control the operation of the imaging system. Digital echo signals are received from the transducer by a communication circuit 130 (e.g. LVDS receiver, Bluetooth, 801.11 or the like) and are provided to receive beamforming electronics 104 that combines echo signals from more than one transducer channel to estimate an echo characteristic for/at a number of locations in the tissue being insonified. Such echo characteristics can be, but are not limited to, the echo amplitude, Doppler phase shift, power spectrum, harmonics or combinations thereof. The outputs of the beamforming electronics 104 are provided to a digital signal processor (DSP) 106 that performs further filtering and signal conditioning of the received echo signals. The outputs of the DSP 106 are provided to a graphics processor unit (GPU) 108 that converts the processed digital echo data into a form that can be displayed on a video display 120. Echo data for images are stored in a frame memory 110 for incorporation into a patient record, for transfer to a patient billing system or for transfer to a remote computer system for storage, review and analysis. The communication circuitry 130 also sends and receives control signals to and from the components in the transducer.

A user interface 132 including one or more of a keyboard, trackball, trackpad, touch sensitive screen, buttons or knobs etc. allow a user to interact with the operating system of the processor 102 to control the functionality of the imaging system. A motion sensor 136 provides a signal to the processor 102 if the imaging system is being moved and/or the angle at which it is being held. Such a motion sensor 136 may comprise an accelerometer or other motion detecting electronics. Finally, a power supply 140 provides electrical power for the imaging system and, in some embodiments, the transducer. The power supply 140 preferably includes one or more rechargeable batteries. As will be appreciated by those skilled in the art, the transducer and base unit may include additional components and details that are not described herein to avoid obscuring the disclosed technology.

As indicated above, the processor 102 of the ultrasound imaging system is programmed to operate the imaging system in one of several power states that draw different levels of power from the power supply 140. A normal operating state is able to draw the most power from the power supply and is used when the imaging system is actively capturing live images of tissue that is in contact with the ultrasound transducer. When the imaging system is idle or not imaging tissue, the processor 102 is programmed to enter one or more lesser power states that reduce the power drawn from the power supply 140 but decrease the functionality of the system and/or the fidelity of the images produced. The processor 102 remains in a lesser power state until it is reactivated according to one or more detected operating conditions of the imaging system as described below.

One problem that occurs with medical devices that operate in a reduced power state is that they can be erroneously awakened by accidental or environmental movements of the device. For example, if an imaging system is transported in a vehicle (e.g. ambulance, first responder vehicle etc.) the device can be jostled. If a motion sensor in the device detects this jostling movement, the device can be erroneously returned to the normal operating state, thereby drawing power from a battery unnecessarily. Such a power draw reduces the standby time of the system and can limit the time that the device can be used for actual patient imaging.

To improve battery management in an ultrasound imaging system, the imaging system of the disclosed technology includes one or more processors that are programmed or operate according to pre-configured logic to awaken and return from a lesser power state to a normal operating state in stages. If the system detects that the imaging system is being used to image tissue, then the processor of the system increases the power used in one or more steps before reaching the normal operating state. However, if the system is not being used to image tissue or meets other defined operating criteria, then the processor can keep the system operating at less than full power. The lesser power state prolongs the battery life and thereby increases the length of time that the device can be used for imaging tissue and the standby time of the system.

Figure 3:
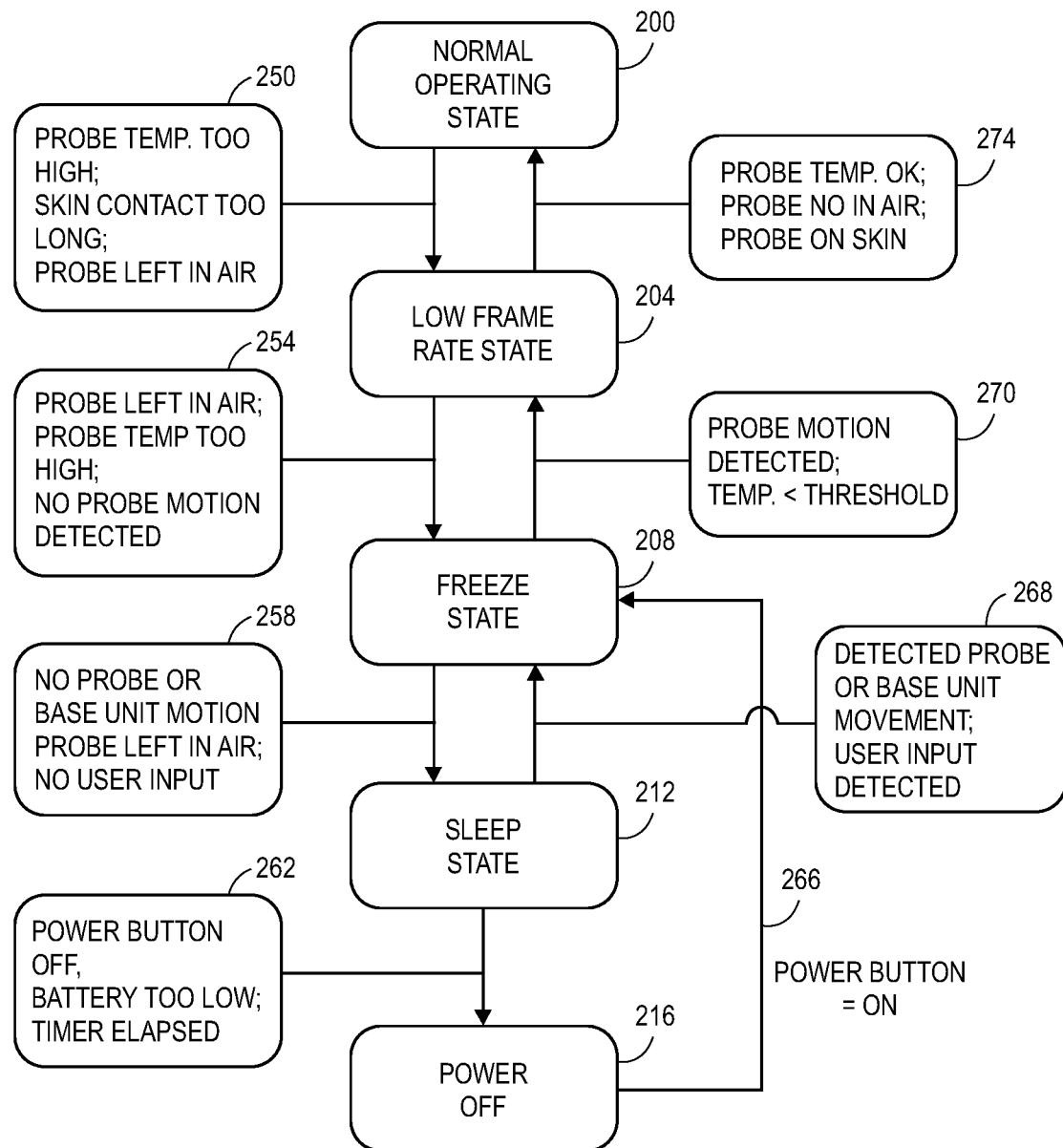
FIG. 3 is a state diagram of a number of different power states used by an ultrasound imaging system in accordance with one embodiment of the disclosed technology.

FIG. 3 shows one exemplary state diagram of a number of different power states that can be used by an ultrasound imaging system to increase battery life in accordance with the disclosed technology. In the embodiment shown, the ultrasound imaging system can operate in five different power states: a normal operating state 200, a low frame rate state 204, a freeze state 208, a sleep state 212 and a power off state 216. The low frame rate state 204, freeze state 208, sleep state 212 and power off state 216 all consume less power (e.g. lessor power states) than the normal operating state 200. As will be appreciated, a greater or lesser number of power states could be implemented that consume different levels of electrical power in accordance with the disclosed technology.

The following table summarizes the capabilities of the imaging system in the different power states in accordance with one embodiment of the disclosed technology. Note that, in this embodiment, the lesser power state comprises at least one of low power state, freeze state, or sleep state:

| Power State | Transmitting/Receiving | Processor | Notes |
|---|---|---|---|
| 1 Normal Operating State | Normal | Normal | Images are taken for examination and other operations of the imaging system are possible. |
| 2 Low Power State* | Low Power | Normal | Not best suited for watching live images. Some operations are not enabled. |
| 3 Freeze State | Stopped | Normal | Live images are not displayed. Some operations are not |

-continued

| Power State | Transmitting/Receiving | Processor | Notes |
| --- | --- | --- | --- |
| 4 Sleep State | Stopped | Standby | enabled. Operations of the imaging system are not possible. Device consumes the lowest power level without being completely off. |
| 5 PowerOff State | Stopped | Stopped | Imaging system is completely off. |

*The low power state comprises at least one of: lower frame rate for transmitting and receiving, lower drive voltages applied or a reduced number of transmit/receive channels used. In the low power state, some imaging modes that require higher power levels such as harmonic Imaging may not be available. Note that one example of the low power state is the low frame rate state 204 discussed above.

In one embodiment, the ultrasound imaging system moves from a current operating state to a power state that consumes less power upon detection of one or more pre-programmed, pre-defined or user-defined operating conditions. Conversely, increasing the power draw from a lesser power state back to the level of the normal operating state is performed in one or more steps so as to increase the power draw more gradually than going, for example, directly from the power off state to the normal operating state.

In one embodiment, the processor 102 in the imaging unit and the microcontroller 62 in the transducer are programmed to detect the pre-programmed, pre-defined or user-defined operating conditions that cause a transition between power states. In one embodiment, transitioning from the normal operating state 200 where the imaging system is actively obtaining and displaying ultrasound data from a region of interest to a low frame rate state 204 that captures ultrasound signals at a lower rate occurs if one or more conditions 250 are met such as the transducer probe temperature being above a set limit (e.g. >41 C) or if the transducer probe has been in contact with a patient's skin for more than a defined limit (e.g. more than 3 minutes without the transducer moving) or if the transducer probe is in the air. If one or more of these conditions are met, a processor 102 transitions the imaging system from the normal operating state to the low frame rate state 204. The processors 102, 62 are programmed to periodically check for these conditions are move the imaging system to a lesser power state if any one of these conditions are detected.

A transition from the low frame rate state 204 where the system is actively acquiring ultrasound data to the freeze state 208 where no new ultrasound data are being acquired but one or more images are still displayed on the video display 120 occurs if one or more conditions 254 are detected. The conditions 254 can include if the transducer probe is left in the air for more than a defined time limit or if the transducer probe temperature exceeds a threshold (e.g. 42.5 C) or if the transducer probe is left touching the skin for more than a defined time limit without any detected movement.

A transition from the freeze state 208 to the sleep state 212 where the system is not acquiring ultrasound data or showing images on a video monitor occurs if any of conditions 258 are detected. These conditions can include if no motion of the transducer probe or the base unit is detected for more than a defined time limit or if the transducer probe has been left in the air for more than a defined time limit or if no user input has been received for more than a defined time limit.

A transition from the freeze state 208 to the power off state 216 where all functions are shut down occurs if one of conditions 262 are detected. Conditions 262 include a power level of a battery dropping below a defined threshold or if a power button has been pressed or activated to an off state or if a timer has elapsed with no movement of the transducer probe or the base unit detected.

In one embodiment of the disclosed technology, a user is required to press or activate a power button before the system will leave the power off state 216. Instead of going directly from the power off state 216 to the normal operating state 200, the system first proceeds to one of the lesser power states such as the freeze state 208 upon detection of the power button being activated.

As indicated, the system does not jump from the power off state 216 directly to the normal operating state 200. Instead a lesser power state such as the freeze state 208 or the low frame rate state 204 is activated first before proceeding to the normal operating state 200. In one embodiment, the power state selected after leaving the power off state is the freeze state 208, whereby one or more images are displayed but no new ultrasound data is acquired. Transition from the freeze state 208 to the low frame rate state 204 occurs if any of conditions 270 are detected. Conditions 270 can include detected motion in the transducer or the main unit or if the temperature of the probe is less than a defined limit (e.g. <42.5 C) or that the probe is not left in the air for more than a defined time limit.

Transition from the low frame rate state 204 to the normal operating state 200 occurs if any of the conditions 274 are detected. Conditions 274 can include if the transducer probe temperature is less than a defined limit (e.g. <41 C) or if the probe is contacting the skin for more than a defined time limit or if the probe is not left in the air. A transition from the sleep state back 212 to the freeze state 208 occurs if any of conditions 268 are detected. Conditions 268 can include detecting movement in the probe or the main unit or if user input on an input control is detected.

As will be appreciated, the particular conditions required to transition from one power state to another may differ from those set forth above. In some embodiments, a user can define conditions such as the time limits or temperature thresholds required for a transition to occur.

On aspect of the disclosed technology is that power is gradually restored to the normal operating state in at least two stages (e.g. power off state to at least one lesser state before proceeding to the normal operating state). Therefore, there is less likelihood that an imaging system will accidently begin operating in the normal operating state if a power button is accidently activated and the unit is not actively positioned to image tissue.

In some embodiments, a low power timer that is not turned off in the power off state keeps track of how long the imaging system is in the power off state. If the time is more than a defined time limit (e.g. >2+ hours), then the imaging system may begin operating in the normal operating state upon power up.

As indicated above, in the low frame rate state 204, imaging still takes place such that the presence of tissue can be detected. However, the system uses less power to image the tissue than can be used in the normal operating state 200. Power can be saved by using less transmit energy (e.g. lowering the transmit voltage) or transmitting at a lower frame rate, using fewer transducer elements, using fewer transmit/receive channels, transmitting on fewer beam lines, using a lower PRF or producing images with less resolution or other adjustments to imaging parameters that reduce the power used. In one embodiment, the processor 102 in the base unit sends commands to the microcontroller 62 in the transducer to control the TX FPGA 68 and/or the TX ASIC 66 so that less power is consumed while imaging tissue. Such imaging may not be optimal for viewing live images but is sufficient to determine if the transducer is imaging tissue versus non-tissue or air.

The freeze state 208 in accordance with one embodiment, stops producing images from the transducer and therefore consumes less power than the low frame rate state 204 but the processor continues to run and is awakened by detecting movement of the transducer or the base unit.

The sleep state 212 further reduces power consumption from the level of the freeze state 208 by disabling the display of images. Images from the transducer are not produced or displayed and further power consuming functions of the system are disabled.

In the power off state, the ultrasound imaging system is completely shut down and in one embodiment is only restarted upon a user pressing or activating the power button.

Examples of conditions that cause the transition from one lesser power state to a higher power state include detecting that the power button has been pressed or detecting movement of the transducer probe, base unit or that the probe is placed on the skin of a subject and that the images of tissue are being obtained. By not proceeding directly from the power off state to the normal operating state, battery drain is minimized and there is less likelihood that the system will be erroneously awakened by jostling or other inadvertent movement. Similarly, power can be increased from the freeze state to the normal operating state by first operating via the low frame rate state. In addition, full transducer power is not used until the system determines that tissue is detected and may provide additional safety for the patient or operator.

Figure 4B:
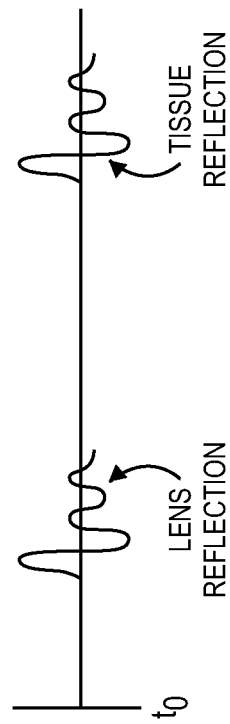
FIGS. 4A and 4B show two exemplary methods of detecting if an ultrasound imaging system is actively imaging tissue or is in the air.
Figure 4A:
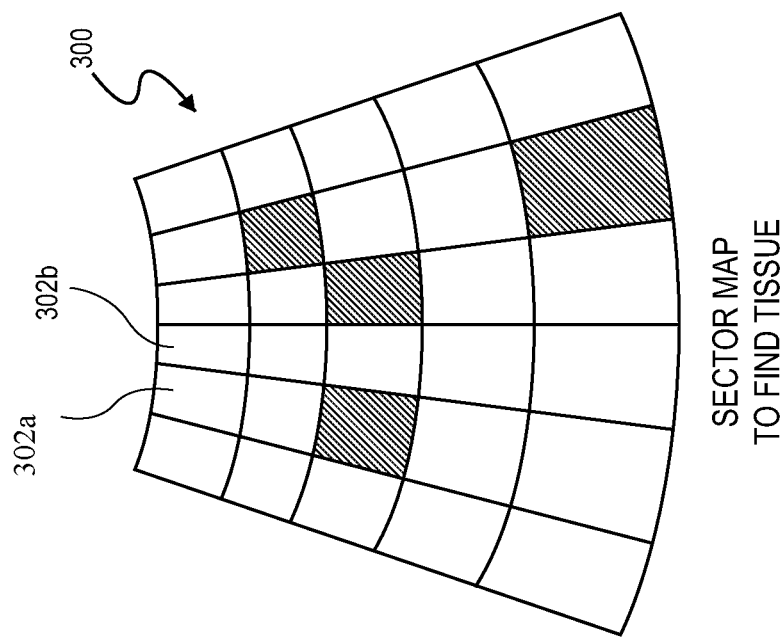

As indicated above, the processor 102 is configured to execute instructions to determine if tissue is detected in the received echo signals. In some embodiments, the processor is programmed to detect variations in one or more echo parameters (e.g. echo intensity) in the field of view of the transducer. As shown in FIG. 4A, a field of view 300 can be divided into a number of sectors 302a, 302b etc. Echo amplitude values for each point in the sectors can be averaged or otherwise combined. If the transducer is placed against a patient's body, then there should be some variation in the echo characteristics in the various sectors depending on the structure of the tissue. If each sector has the same (or nearly the same e.g. +1-5 dB) average amplitude value, then it is likely that the transducer is not placed against a body and the transducer is imaging free space or other non-tissue object. Therefore, in one embodiment, the processor is programmed to detect tissue in an image based on the detected variations in echo characteristics in a received ultrasound frame. As will be appreciated, different intensity thresholds or detecting tissue may be applied if the system is operating in the normal operating state versus a lesser power state because of the reduced transmit voltages, decreased number of channels, lower PRF etc. so that the same test used to identify tissue in the normal power state may not be used to identify tissue in a lesser power state.

In yet another embodiment, a return time of the echo signals can be used to determine if the transducer is placed against an object or is imaging free space. As shown in FIG. 4B, a transducer will receive a first echo signal from a lens surface due to the mismatch of acoustic impedance between the lens and the surrounding medium (e.g. air). Tissue will produce a second echo at some point in time after the lens reflection. If no tissue reflection occurs, then the processor can determine that the transducer is likely imaging free space and can enter a lesser power state.

Embodiments of the subject matter and the operations described in this specification can be implemented in digital electronic circuitry, or in software, firmware, or hardware, including the structures disclosed in this specification and their structural equivalents, or in combinations of one or more of them. Embodiments of the subject matter described in this specification can be implemented as one or more programs, i.e., one or more modules of program instructions, encoded on non-transitory computer storage medium for execution by, or to control the operation of, data processing apparatus.

The term "processor" encompasses all kinds of apparatus, devices, and machines for processing data, including by way of example a programmable processor, microcontroller, a computer, a system on a chip, or multiple ones, or combinations, of the foregoing. The processor can include special purpose logic circuitry, e.g., an FPGA (field programmable gate array) or an ASIC (application-specific integrated circuit). The processor also can include, in addition to hardware, computer program code that creates an execution environment for the computer program in question, e.g., code that constitutes processor firmware.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit). Generally, a processor will receive instructions and data from a read-only memory or a random access memory or both.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. An ultrasound imaging system comprising:
a transducer configured to deliver an ultrasound energy to an object and to detect echo signals from the object; and
a processor coupled to the transducer, the processor implemented to configure the ultrasound imaging system in a power off state, a first operating state, and a second operating state that consumes less power than the first operating state;
wherein the transducer is configured to operate, upon transition of the ultrasound imaging system from the power off state to the first operating state, at a first power in the first operating state and at a second power in the second operating state that is less than the first power, wherein the transducer is configured to operate at the second power in the second operating state by using one or more of a reduced transmit power, a lower frame rate or a lower pulse repetition frequency compared to operating at the first power in the first operating state.

2. The ultrasound imaging system of claim 1, wherein the processor is configured to:
   determine that the object has not been imaged in a first defined time limit or that the imaging system or the transducer has not been moved in a second defined time limit; and
   switch, responsive to said determine, the ultrasound imaging system to the second operating state.

3. The ultrasound imaging system of claim 1, wherein the processor is configured to prevent use of one or more ultrasound imaging modes while the ultrasound imaging system is operating in the second operating state.

4. The ultrasound imaging system of claim 1, wherein the transducer includes a temperature sensor configured to detect a temperature of the transducer and the processor is configured to switch the ultrasound imaging system to the second operating state if the temperature exceeds a threshold.

5. The ultrasound imaging system of claim 1, wherein the transducer includes a temperature sensor configured to detect a temperature of the transducer and the processor is configured to prevent transition of the ultrasound imaging system to the first operating state if the temperature exceeds a threshold.

6. The ultrasound imaging system of claim 1, wherein the processor is configured to:
   determine that the transducer is imaging in air for a defined time limit; and
   switch, responsive to said determine, the ultrasound imaging system to the second operating state.

7. The ultrasound imaging system of claim 1, wherein when the ultrasound imaging system is in the second operating state, the transducer uses fewer transmit elements than when the ultrasound imaging system is in the first operating state.

8. The ultrasound imaging system of claim 1, wherein when the ultrasound imaging system is in the second operating state, the transducer uses fewer beam lines than when the ultrasound imaging system is in the first operating state.

9. The ultrasound imaging system of claim 1, wherein the processor is configured to:
   determine that ultrasound images generated by the ultrasound imaging system do not include the object in a defined time limit; and
   switch, based on said determine, the ultrasound imaging system to the second operating state.

10. An ultrasound imaging system comprising:
    a transducer configured to deliver an ultrasound energy to an object and to receive echo signals from the object; and
    a processor coupled to the transducer that is configured to operate the ultrasound imaging system in a first power state and operate the ultrasound imaging system in a second power state upon transition from a power off state, wherein the transducer in the second power state is implemented to receive the echo signals at less power than in the first power state.

11. The ultrasound imaging system of claim 10, wherein a transmit power of the transducer in the second power state is lower than the transmit power in the first power state.

12. The ultrasound imaging system of claim 10, wherein the processor is configured to:
    determine that the object has not been imaged by the ultrasound imaging system in a predetermined time; and
    configure, responsive to said determine, the ultrasound imaging system for operation in the second power state.

13. The ultrasound imaging system of claim 10, further comprising a motion sensor configured to detect a motion of the ultrasound system, wherein the processor is configured to switch the ultrasound imaging system from a third power state to the second power state based on the motion, wherein the ultrasound imaging system consumes more power in the second power state than in the third power state.

14. The ultrasound imaging system of claim 10, further comprising a temperature sensor configured to determine a temperature of the transducer, wherein the processor is implemented to:
    configure, when the temperature exceeds a first threshold, the ultrasound imaging system for operation in the second power state; and
    configure, when the temperature exceeds a second threshold that is different than the first threshold, the ultrasound imaging system for operation in a third power state in which the ultrasound imaging system consumes less power than in the second power state.

15. The ultrasound imaging system of claim 10, wherein the processor is configured to:
    determine that the transducer has been imaging in air for a predetermined time; and
    configure, responsive to said determine, the ultrasound imaging system for operation in the second power state.

16. The ultrasound imaging system of claim 10, wherein when the ultrasound system operates in the second power state, the transducer uses at least one fewer transmit elements or fewer beam lines for imaging than when the ultrasound system operates in the first power state.

17. A method implemented by an ultrasound imaging system, the method comprising:
    receiving a request to transition the ultrasound imaging system from a power off state, the ultrasound imaging system operable in a first operating state and a second operating state upon transition from the power off state, the ultrasound imaging system consuming less power in the second operating state than in the first operating state;
    determining, with a processor of the ultrasound imaging system, a next state of the ultrasound imaging system as the first operating state or the second operating state; and
    activating, with the processor, a transducer of the ultrasound imaging system in the next state to deliver an ultrasound energy to an object and to detect echo signals from the object, the transducer operating to receive the echo signals at a first power when the next state is the first operating state and to receive the echo signals at a second power when the next state is the second operating state, the second power being less than the first power.

18. The method of claim 17, further comprising determining an amount of motion of the transducer, wherein the determining the next state is based on the amount of motion.

19. The method of claim 17, further comprising:
    determining an event occurrence when the ultrasound imaging system is in the power off state, the event occurrence selected from the group consisting of an expiration of a timer and an activation of a power button; and transitioning the ultrasound imaging system to the next state responsive to the determining the event occurrence.

* * * * *